United States Patent

Buchecker et al.

[11] Patent Number: 5,888,423
[45] Date of Patent: Mar. 30, 1999

[54] FLUOROBENZYL ETHER DERIVATIVES

[75] Inventors: Richard Buchecker, Zurich; Alfred Germann, Basel, both of Switzerland

[73] Assignee: Rolic Ag, Zug, Switzerland

[21] Appl. No.: 667,686

[22] Filed: Jun. 21, 1996

[30] Foreign Application Priority Data

Jul. 17, 1995 [CH] Switzerland .............. 2096/95

[51] Int. Cl.⁶ .......... C09K 19/30; C09K 19/12; C09K 19/34; C07C 41/00
[52] U.S. Cl. .............. 252/299.63; 252/299.61; 252/299.66; 568/647
[58] Field of Search ........ 252/299.63, 299.61, 252/299.66; 568/647; 549/369

[56] References Cited

U.S. PATENT DOCUMENTS

| | | | |
|---|---|---|---|
| 4,565,425 | 1/1986 | Petrzilka et al. | 252/299.5 |
| 5,013,477 | 5/1991 | Buchecker et al. | 252/299.63 |
| 5,102,578 | 4/1992 | Buchecker et al. | 252/299.63 |
| 5,180,519 | 1/1993 | Uchida et al. | 252/299.63 |
| 5,230,826 | 7/1993 | Boller et al. | 252/299.61 |
| 5,366,659 | 11/1994 | Tsai et al. | 252/299.61 |
| 5,372,746 | 12/1994 | Buchecker et al. | 252/299.61 |
| 5,399,282 | 3/1995 | Buchecker et al. | 252/299.63 |
| 5,458,805 | 10/1995 | Wachtler et al. | 252/299.63 |

FOREIGN PATENT DOCUMENTS

| | | |
|---|---|---|
| 0 122 389 | 2/1984 | European Pat. Off. . |
| 0 315 014 | 10/1988 | European Pat. Off. . |
| 0 543 244 | 11/1992 | European Pat. Off. . |
| 543 244 A1 | of 1993 | European Pat. Off. . |
| A-42 22 371 A1 | of 1994 | Germany . |
| A 44 25 642 A1 | of 1996 | Germany . |

OTHER PUBLICATIONS

Derwent Database WPI Abstract Accession No. C94–136628 of Kanto, Japanese Patent Document No. JP 06 228 037 (1994).
Derwent Database WPI Abstract Accession No. C96–022389 of Naito, et al., International PCT Application Publication No. WO 96–00204 (1996).
Chem. Abs 122: 278263, Jul. 1994.
Liquid Crystals, 1993, vol. 13 (3), pp. 345–351, 1993.
Molecular Crystals Liquid Crystals 131, pp. 109–123 and pp. 327–342 (1985).
Tetrahedron Letters 35, 3277–3280 (1994).

*Primary Examiner*—C. H. Kelly
*Attorney, Agent, or Firm*—Bryan Cave LLP

[57] ABSTRACT

Flourobenzyl ether derivatives of the formula

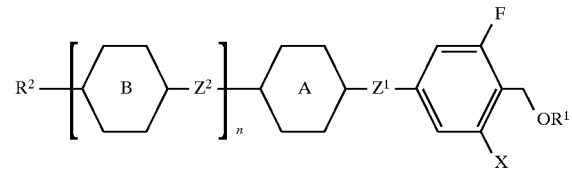

and liquid crystalline mixtures which contain such compounds are prepared and employed in electro-optical display devices.

12 Claims, No Drawings

FLUOROBENZYL ETHER DERIVATIVES

FIELD

The invention relates to fluorobenzyl ether derivatives, liquid crystalline mixtures which contain such compounds and the use of such compounds and mixtures in electro-optical devices.

BACKGROUND

Liquid crystals are used primarily as dielectrics in display devices, since the optical properties of such substances can be influenced by an applied voltage. Electro-optical devices based on liquid crystals will be well-known to a person skilled in the art and can be based on various effects. Such devices are, for example, cells having dynamic scattering, DAP cells (deformation of aligned phases), guest/host cells, TN cells having a "twisted nematic" structure, STN cells ("super twisted nematic"), SBE cells ("super birefringence effect") and OMI cells ("optical mode interference"). For displays having a high content of information, actively controlled cells, e.g. TFT cells ("thin film transistor"), have in particular recently become important in addition to passively controlled, multiplexed cells. The most common indicating devices are based on the Schadt-Helfrich effect and have a twisted nematic structure.

The liquid crystal materials must have a good chemical, photochemical and thermal stability and a good stability towards electric fields. Further, they should have a suitable mesophase over a range which is as broad as possible (for example, a nematic or a cholesteric phase for the cells referred to above), but in spite of a sufficiently low viscosity should permit short response times, low threshold potentials and a high contrast in the cells. Further properties such as the electrical conductivity, the dielectric anisotropy and the optical anisotropy must fulfill different requirements depending on the field of application and type of cell. For example, materials for cells having a twisted nematic structure should have a positive dielectric anisotropy which is as high as possible and at the same time should have a conductivity which is as low as possible. This latter property is of particular importance primarily for TFT cells. Unfortunately, however, components having a high dielectric anisotropy mainly lead to an increased conductivity in mixtures because of their increased capacity to dissolve ionic impurities. Accordingly, components which are distinguished by a dielectric anisotropy which is as high as possible with simultaneously a conductivity which is as low as possible are sought after.

SUMMARY OF THE INVENTION

The invention relates to compounds of the general formula

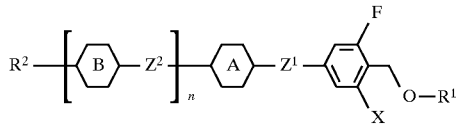

wherein

R$^1$ is C$_1$–C$_5$-alkyl or C$_3$–C$_5$-alkenyl; C$_3$–C$_5$ alkyl or C$_3$–C$_5$ alkenyl in which one CH$_2$ group is replaced by an oxygen atom; C$_1$–C$_5$ alkyl or C$_3$–C$_5$ alkenyl in which at least one hydrogen atom is replaced by a fluorine atom; or C$_1$–C$_5$ alkyl or C$_3$–C$_5$ alkenyl in which one CH$_2$ group is replaced by an oxygen atom and in which at least one hydrogen atom is replaced by a fluorine atom;

X is H or F;

A and B each independently is trans-1,4-cyclo-hexylene, trans-1,3-dioxane-2,5-diyl, pyridine-2,5-diyl, pyrimidine-2,5-diyl, 1,4-phenylene or 1,4-phenylene substituted with 1 or 2 fluorine atoms;

Z$_1$ and Z$_2$ each independently is a single bond, —CH$_2$—CH$_2$—, —O—CH$_2$—, —CH$_2$—O—, —C≡C—, —(CH$_2$)$_4$—, —O(CH$_2$)$_3$—, —(CH$_2$)$_3$O—, —CH=CH—CH$_2$O— or —CH=CH—(CH$_2$)$_2$—, and Z$^2$ also is —OCH$_2$—CH=CH— or —(CH$_2$)$_2$—CH=CH—; wherein at least one of groups Z$^1$ and Z$^2$ is a single bond;

n is 0 or 1; and

R$^2$ is C$_2$–C$_{12}$-alkyl or C$_2$–C$_{12}$-alkenyl; C$_2$–C$_{12}$ alkyl or C$_2$–C$_{12}$ alkenyl in which one or more non-adjacent CH$_2$ groups is replaced by oxygen; C$_2$–C$_{12}$ alkyl or C$_2$–C$_{12}$ alkenyl in which one or more hydrogen atoms is replaced by a fluorine atom; or C$_2$–C$_{12}$ alkyl or C$_2$–C$_{12}$ alkenyl in which one or more non-adjacent CH$_2$ groups is replaced by an oxygen atom and in which one or more hydrogen atoms is replaced by a fluorine atom.

The compounds in accordance with the invention, which are distinguished by low melting points and comparatively high clearing points, have, in spite of low polarity, a comparatively low threshold potential (V$_{10}$) and are therefore especially suitable for use in TFT cells.

DETAILED DESCRIPTION OF THE INVENTION

R$^1$ embraces in the scope of the present invention straight-chain alkyl groups such as methyl, ethyl, propyl, butyl, pentyl; straight-chain alkoxyalkyl groups such as methoxymethyl, methoxyethyl; straight-chain alkenyl groups such as 3E-pentenyl, 2-propenyl, 3-butenyl, 4-pentenyl; alkenyloxyalkyl groups and the like.

R$_2$ embraces in the scope of the present invention straight-chain alkyl groups such as methyl, ethyl, propyl, butyl, pentyl, hexyl, heptyl, octyl, nonyl, decyl, undecyl, dodecyl; alkoxy groups in which the alkyl residue is as defined above; alkoxyalkyl groups such as, for example, methoxymethyl, ethoxymethyl, propyloxymethyl, methoxyethyl, ethoxyethyl, propoxyethyl; 1-alkenyl groups such as 1E-propenyl, 1E-butenyl, 1E-pentenyl, 1E-hexenyl, 1E-heptenyl; 3-alkenyl groups such as 3E-pentenyl, 3E-hexenyl, 3E-heptenyl, alkenyl groups having a terminal double bond such as vinyl, 2-propenyl, 3-butenyl, 4-pentenyl, 6-hexenyl; alkenyloxy groups such as 2E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy, 7-octenyloxy, 8-nonenyloxy, 9-decenyloxy, 10-undecenyloxy, 11-dodecenyloxy; fluorinated groups such as fluoromethyl, difluoromethyl, trifluoromethyl, 1-fluoropropyl, 1-fluoropentyl, 1-chloropropyl, 2-fluoropropyl, 2-fluoropentyl, 2-chloropropyl, 2-fluoropropyloxy, 2-fluorobutyloxy, 2-fluoropentyloxy, 2-fluorohexyloxy, and the like.

Especially preferred compounds of formula I are those in which R$^1$ has 1 to 3 carbon atoms and signifies methyl, ethyl or propyl, especially methyl. R$^2$ preferably has 2 to 6 carbon atoms and signifies ethyl, propyl, butyl, pentyl, hexyl, vinyl, 1E-propenyl, 1E-butenyl, 1E-pentenyl, 1E-hexenyl, 3-butenyl or 4-pentenyl. Z$^1$ and Z$^2$ preferably signify a single bond or —CH$_2$CH$_2$—; and rings A and B preferably signify trans-1,4-cyclohexylene, trans-1,3-dioxane-2,5-diyl or 1,4-phenylene.

Especially preferred compounds of formula I are accordingly the compounds of the general formulae

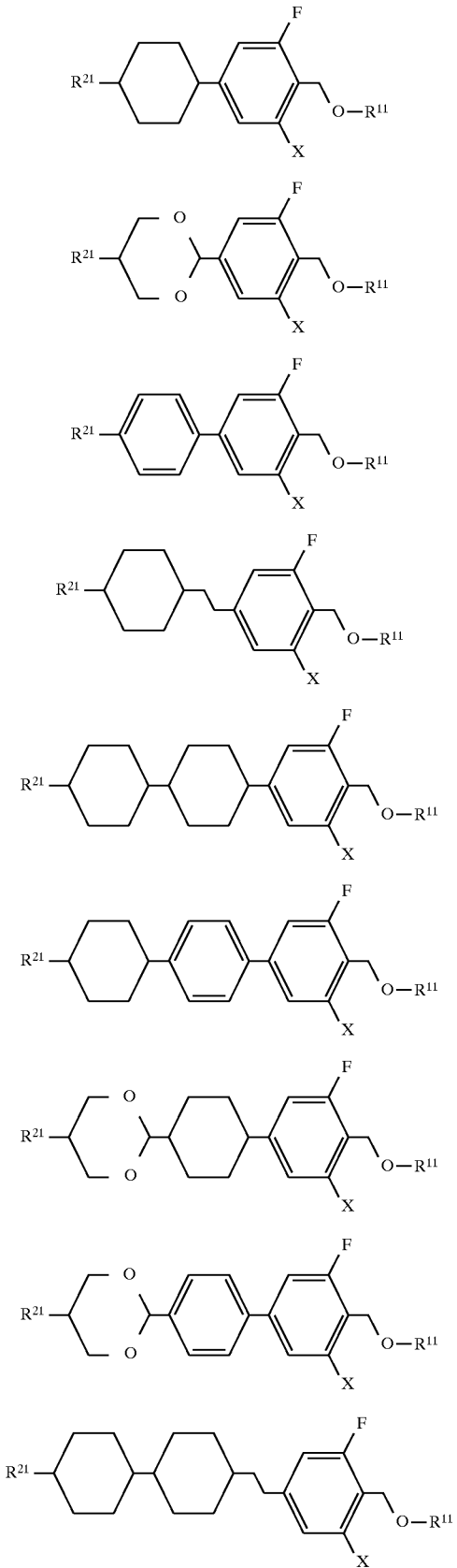

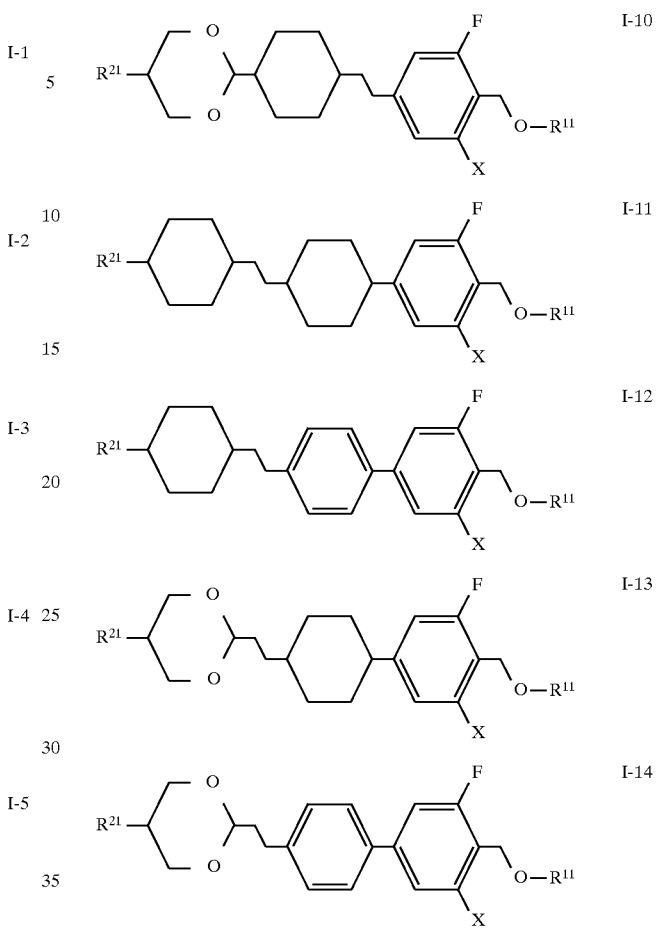

wherein
$R^{11}$ signifies $C_1$–$C_3$-alkyl;
X H or F; and
$R^{21}$ signifies $C_2$–$C_6$-alkyl or $C_2$–$C_6$-alkenyl.

The compounds of general formula I can be produced in a known manner as outlined in Scheme 1. For example, nitriles of general formula 1, can be converted by acidic hydrolysis into the corresponding acids 3. Subsequent reduction of the acids 3 to the alcohols 4a–4g and etherification of 4a with an alkyl bromide or alkyl iodide leads directly to the compounds of formula 1, while etherification of the alcohols 4b–4g leads to the intermediates of formula 5b–5g. Further, the acids of general formula 3 can also be obtained from 3-fluoro- or 3,5-difluorophenyl derivatives of formula 2, by deprotonation in the 4-position and subsequent carboxylation with $CO_2$.

By acidic hydrolysis of the acetals or enol ethers of formulae 4b–4g there are liberated initially the corresponding ketones or aldehydes; those compounds of formula I in which $R^2$ signifies alkyl can then be produced by Wittig olefination, subsequent hydrogenation and etherification. For the production of the compounds of formula I in which $R^2$ signifies alkenyl, transformation into the benzyl ether 5b–5g is firstly carried out prior to—as in the case of the compounds of formula 4b–4g—the acidic hydrolysis. The aldehydes or ketones which are thereby obtained can be subsequently homologized one or more times depending on the desired position of the double bond optionally by a Wittig reaction with methoxymethyl-triphenyl-phosphonium salts and subsequent hydrolysis of the enol ethers formed. The aldehydes can be converted into the desired olefins of formula I by reaction with alkyltriphenylphosphonium salts. The compounds of formula I in which ring B represents 1,3-dioxane-2,5-diyl can be produced in the usual manner by acetal formation of the aldehydes formed from 5 c, 5d or 5f with a 2-alkyl-1,3-propanediol or an analogous alkenyl-1,3-propanediol. The mentioned reactions starting from 4b–4g or 5b–5g are known and have been described in literature on liquid crystal chemistry, for example in EP-A-0 1 22 389 or in Molecular Crystals Liquid Crystals 131, page 109 et. seq. or page 327 et. sec. (1985).

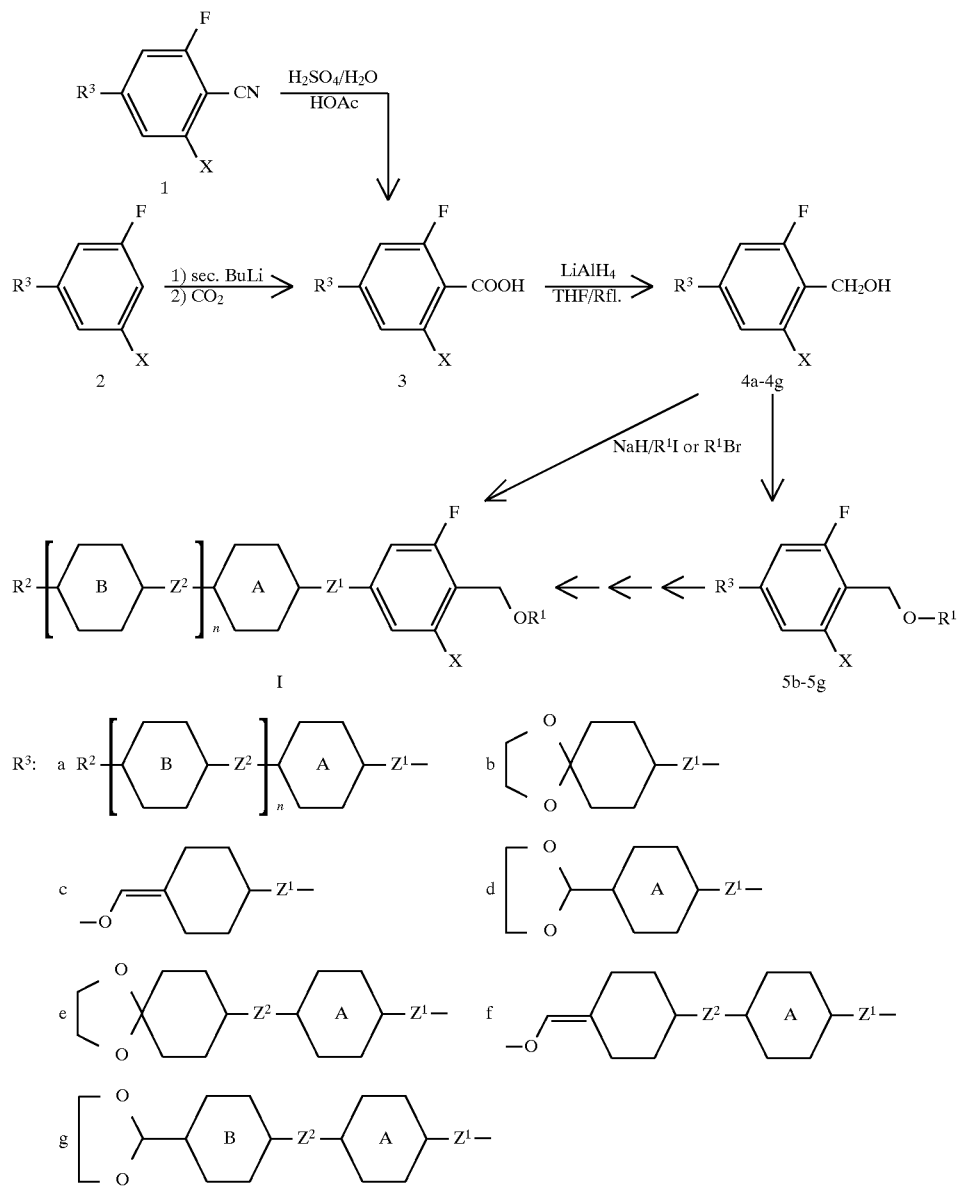

Scheme 1

The production of the compounds of the general formula I in which ring A represents an aromatic ring can be effected, for example, by a palladium-catalyzed coupling of a boric acid derivative with an aromatic bromide, iodide or also perfluoroalkylsulphonate (e.g. trifluoromethylsulphonate) as set forth in Scheme 2. Such couplings have been described, for example, in Tetrahedron Letters 35, 3277 (1994).

Scheme 2

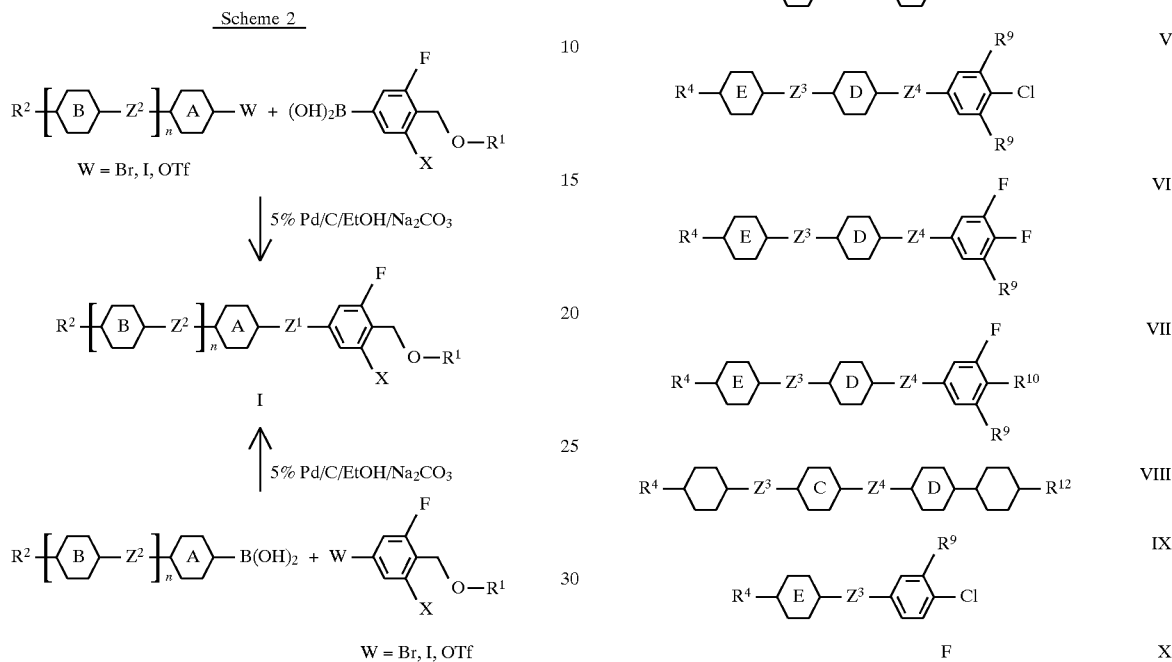

The starting materials required for the synthesis of the compounds of formula I are known or are analogues of known compounds. Thus, for example, nitriles of formula 1 have been described as liquid crystals. 3-Fluorophenyl or 3,5-difluorophenyl derivatives of formula 2 have been described as such, as isomers or also analogous phenyl fluorides, for example in EP-A-0 31 5 014 or EP-A-0 543 244.

The compounds of formula I can be used in the form of mixtures with one another and/or with other liquid crystal components. The invention is therefore also concerned with liquid crystalline mixtures having at least two components, wherein at least one component is a compound of formula 1. A second component and any additional components can be further compounds of general formula I or other suitable liquid crystal components. Suitable liquid crystal components will be known in large numbers to a person skilled in the art, e.g. from D. Demus et al., Flüssige Kristalle in Tabellen, VEB Deutscher Verlag fur Grundstoffindustrie, Leipzig, volumes I and II, or from Landolt-Börnstein, Liquid Crystals, volume IV 7a–d, many of then are, moreover, commercially available.

Having regard to the good solubility of the compounds of formula I in accordance with the invention in other liquid crystal materials and having regard to their good miscibility with one another, the content of compounds of formula I in the mixtures in accordance with the invention can be relatively high and can be, for example, 1–70 wt. %. In general, a content of about 3–40 wt. %, especially of about 5–20 wt. %, of compounds of formula I is preferred.

Preferably, the mixtures in accordance with the invention contain, in addition to one or more compounds of formula I, one or more compounds from the group of compounds of the formulas

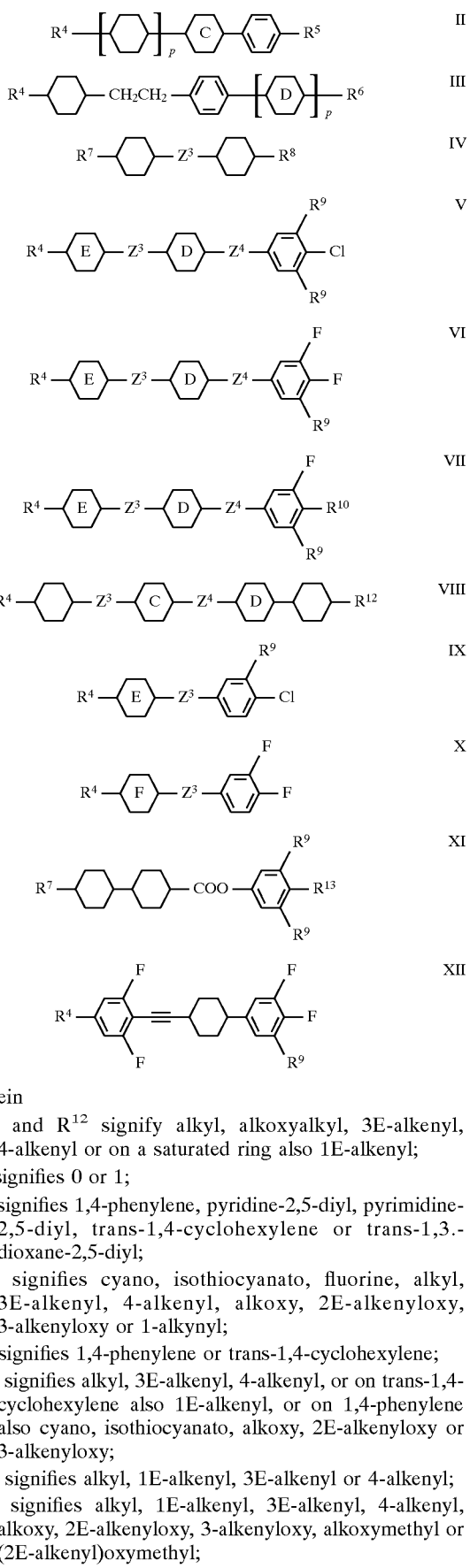

wherein $R^4$ and $R^{12}$ signify alkyl, alkoxyalkyl, 3E-alkenyl, 4-alkenyl or on a saturated ring also 1E-alkenyl;

p signifies 0 or 1;

C signifies 1,4-phenylene, pyridine-2,5-diyl, pyrimidine-2,5-diyl, trans-1,4-cyclohexylene or trans-1,3.-dioxane-2,5-diyl;

$R^5$ signifies cyano, isothiocyanato, fluorine, alkyl, 3E-alkenyl, 4-alkenyl, alkoxy, 2E-alkenyloxy, 3-alkenyloxy or 1-alkynyl;

D signifies 1,4-phenylene or trans-1,4-cyclohexylene;

$R^6$ signifies alkyl, 3E-alkenyl, 4-alkenyl, or on trans-1,4-cyclohexylene also 1E-alkenyl, or on 1,4-phenylene also cyano, isothiocyanato, alkoxy, 2E-alkenyloxy or 3-alkenyloxy;

$R^7$ signifies alkyl, 1E-alkenyl, 3E-alkenyl or 4-alkenyl;

$R^8$ signifies alkyl, 1E-alkenyl, 3E-alkenyl, 4-alkenyl, alkoxy, 2E-alkenyloxy, 3-alkenyloxy, alkoxymethyl or (2E-alkenyl)oxymethyl;

$Z^3$ and $Z^4$ signify a single bond or —CH$_2$CH$_2$—, with two aromatic rings always being linked by a single bond;

E signifies trans-1,4-cyclohexylene or trans-1,3-dioxane-2,5-diyl;

$R^9$ signifies hydrogen or fluorine;

$R^{10}$ signifies difluoromethoxy or trifluoromethoxy;

$R^{13}$ signifies cyano, fluorine, chlorine, difluoromethoxy or trifluoromethoxy; and F signifies pyrimidine-2,5-diyl, trans-1,4-cyclohexylene or trans-1,3-dioxane-2,5-diyl.

The terms alkyl, alkyloxy, 1E-alkenyl, 3E-alkenyl and alkenyl having a terminal double bond used in connection with the compounds of formulae II to XVI are defined in more detail above;

"4-alkenyl" preferably signifies straight-chain alkenyl residues with a maximum of 12 carbon atoms in which the double bond is situated in the 4-position, such as, for example, 4-pentenyl, 4-hexenyl or 4-heptenyl;

"aromatic rings" signifies rings such as, for example, 1,4-phenylene, pyridine-2,5-diyl or pyrimidine-2,5-diyl;

"saturated rings" signifies trans-1,4-cyclohexylene or-trans-1,3-dioxane-2,5-diyl;

"alkyloxyalkyl" preferably signifies straight-chain residues with a maximum of 12 carbon atoms such as, for example, methoxymethyl, ethoxymethyl, propyloxymethyl, butyloxymethyl and the like;

"2E- or 3-alkenyloxy" preferably signifies straight-chain alkenyloxy residues with a maximum of 12 carbon atoms in which the double bond is situtated in the 2- or 3-position and E or Z indicates the preferred configuration, such as, for example, allyloxy, 2E-butenyloxy, 2E-pentenyloxy, 2E-hexenyloxy, 2E-heptenyloxy, 3-butenyloxy, 3-pentenyloxy, 3-hexenyloxy, 3-heptenyloxy, 4-pentenyloxy, 5-hexenyloxy, 6-heptenyloxy and the like;

"1-alkynyl" preferably signifies straight-chain alkynyl residues with a maximum of 12 carbon atoms in which the triple bond is situated in the 1-position, such as, for example, ethynyl, 1-propynyl, 1-butynyl, 1-pentynyl and the like.

The mixtures in accordance with the invention can also contain optically active compounds (e.g. optically active 4'-alkyl- or 4'-alkoxy-4-biphenylcarbonitriles) and/or dichroic dyes (e.g. azo, azoxy or anthraquinone dyes). The content of such compounds is determined by the solubility, the desired helical pitch, colour, extinction and the like. In general, the content of optically active compounds and dichroic dyes is a maximum of in each case about 10 wt. % in the final mixture.

The production of the liquid crystalline mixtures and of the electro-optical devices can be effected in a known manner.

The production of the compounds of formula I and of liquid crystalline mixtures containing these compounds are illustrated in more detail by the following Examples. C signifies a crystalline phase, S signifies a smectic phase, N signifies a nematic phase and I signifies the isotropic phase. $V_{10}$ denotes the voltage for 10% transmission (viewing direction perpendicular to the plate surface). $t_{on}$ and $t_{off}$ denote, respectively, the switching-on time and the switching-off time and An denotes the optical anisotropy.

EXAMPLE 1 a) A solution of 109 g of 1-bromo-3-fluorobenzene in 270 ml of dry tetrahydrofuran was slowly added dropwise to 14.4 g (0.623 mol) of magnesium shavings and a spatula tip of iodine crystals in such a manner that the reaction mixture was held at the reflux temperature. The reaction mixture was left at 73°–75° C. until the magnesium had been consumed completely, then cooled to 5° C. and treated within 20 minutes with a solution of 117.2 g of 4-(1,4-dioxaspiro[4,5]dec-8-yl)cyclohexanone in 460 ml of anhydrous tetrahydrofuran at 5°–15° C. Thereafter, the reaction solution was warmed to room temperature -and stirred for 90 minutes. Subsequently, 800 ml of 10 percent ammonium chloride solution were added dropwise in such a manner that the temperature did not exceed 35° C. The reaction mixture was thereupon extracted with ether, the organic phase was dried over sodium sulfate, filtered and the filtrate was evaporated. This gave 174.3 g of crude 4-(1,4-dioxaspiro[4,5]dec-8-yl)-1-(3-fluorophenyl)cyclohexanol as brownish crystals which were used in the next reaction without further purification. (cis/trans: 47.5:49.5).

b) A mixture of 174.3 g of 4-(1,4-dioxaspiro[4,5]dec-8-yl)-1-(3-fluorophenyl)cyclohexanol, 1000 ml of 1,2-dichloroethane, 25 ml of ethylene glycol and 25 g of Amberlyst 15 was boiled under reflux for 22 hrs., the condensate being dried over a dropping funnel filled with 175 g of neutral aluminiumoxide. Then, the reaction mixture was cooled, filtered, washed with water and the organic phase was dried over sodium sulphate. Subsequent chromatography on 1000 g of silica gel with hexane/ethyl acetate (90:1) gave 124.2 g of 4-(1,4-dioxaspiro[4,5]dec-8-yl)-1-(3-fluorophenyl)-cyclohexene as colorless crystals. M.p. of a sample recrystallized from methylene chloride/hexane: 133.7°–135.3° C.

c) A solution of 4-(1,4-dioxaspiro[4,5]dec-8-yl)-1-(3-fluorophenyl)cyclohexene in 21 of toluene was hydrogenated using 10% Pd/C at room temperature and under normal pressure until 12.41 of hydrogen had been taken up. The reaction mixture was thereupon filtered and the filtrate was evaporated. This gave 125.3 g of 4-(1,4-dioxaspiro[4,5]dec-8-yl)-1-(3-fluorophenyl)-cyclohexane as a yellowish oil (cis/trans 50/47).

d) 23.7 g of potassium t.-butylate were added to a solution of 125.3 g of 4-(1,4-dioxaspiro[4,5]dec-8-yl)-1-(3-fluorophenyl)-cyclohexane (cis/trans 50/47) in 630 ml of dimethyl sulphoxide, the mixture was stirred at 100° C. for 2 hrs., cooled and poured into 2500 ml of 5 percent sodium chloride solution. The reaction mixture was extracted with methylene chloride, the organic phase was dried over sodium sulfate, filtered and the filtrate was evaporated. Crystallization of the residue from isopropanol gave 121.9 g of trans-4-(1,4-dioxaspiro[4,5]dec-8-yl)-1-(3-fluorophenyl) cyclohexane as colorless crystals (trans content 99.8%).

e) A solution of 6.3 g of trans-4-(1,4-dioxaspiro[4,5]dec-8-yl)-1-(3-fluorophenyl)cyclohexane and 2.317 g of N,N,N', N'-tetra-methyl-ethylenediamine (TMEDA) in 50 ml of dry tetrahydrofuran was treated at −75° C. under argon within 15 min. with 25 ml (32.5 mmol) of a sec. butyllithium solution. Then, the mixture was left to react at the same temperature for 2.5 hrs. During this time sufficient solid carbon dioxide was introduced into 300 ml of ether such that the weight increase of the solution was 40 g. The tetrahydrofuran solution was introduced into this ether solution under pressure using a catheter, with the temperature rising to −52° C. The reaction mixture was warmed to 0° C. and treated cautiously with 100 ml of ice-cold 1N hydrochloric acid and subsequently 200 ml of ice-water, extracted with methylene chloride, the organic phase was dried over sodium sulfate, filtered and the filtrate was evaporated. The residue was crystallized from acetone/hexane. This gave 3.4 g of 4-[trans-4-(1,4-dioxaspiro[4,5]dec-8-yl)cyclohexyl]-2-fluorobenzoic acid as yellowish crystals (m.p. 227.8° C.; dec.).

f) 5.7 g of 4-[trans-4-(1,4-dioxaspiro[4,5]dec-8-yl) cyclohexyl]-2-fluorobenzoic acid were added to a suspension of 3 g of lithium aluminium hydride in 100 ml of dry ether and, after stirring under reflux for 23 hrs., cooled to 0° C., treated cautiously with 25 ml of water and then 100 ml of 3N sulfuric acid. The reaction mixture was thereupon extracted with ether, the organic phase was dried over sodium sulfate, filtered and the filtrate was evaporated. Chromatography of the residue on silica gel with methylene chloride/acetone (95:5) gave 3.1 g of 4-[trans-4-(1,4-dioxaspiro[4,5]dec-8-yl)cyclohexyl]-2-fluorobenzyl alcohol as colorless crystals.

g) A solution of 3.1 g of 4-[trans-4-(1,4-dioxaspiro-[4,5] dec-8-yl)cyclohexyl]-2-fluorobenzyl alcohol in 100 ml of toluene and 40 ml of formic acid was stirred at room temperature for 4 hours, poured into water, extracted with toluene, the organic phases were combined, washed with 10% sodium bicarbonate, dried over sodium sulfate, filtered and the filtrate was evaporated. This gave 3.06 g of crude 4-[trans-4-(4-oxocyclohexyl)cyclohexyl]-2-fluorobenzyl formate of 99% purity (GC).

h) 2.7 g of potassium t.-butylate were added to a suspension of 6.6 g of methoxymethyltriphenylphosphonium chloride in 40 ml of t.-butyl methyl ether at −15° C. and the mixture was stirred for one hour. Then, the mixture was diluted at 0° C. with 20 ml of t.-butyl methyl ether and thereupon a solution of 3.88 g of 4-[trans-4-(4-oxocyclohexyl)cyclohexyl]-2-fluorobenzyl formate in 40 ml of tetrahydrofuran was added dropwise during 50 minutes. After a further 2 hours at 0° C. the reaction solution was poured into water and the mixture was extracted with methylene chloride. The organic phase was dried over sodium sulfate, filtered and the filtrate was concentrated. The residue was chromatographed on silica gel with methylene chloride/acetone (98:2). This gave 0.69 g of 4-[trans-4-(4-methoxymethylidenecyclohexyl)cyclohexyl]-2-fluorobenzyl alcohol in addition to 1.82 g of 4-[trans-4-(4-oxocyclohexyl)cyclohexyl]-3-fluorobenzyl alcohol, which could be re-used.

i) 0.4 g of sodium hydride dispersion (in oil, about 50 percent) was washed with hexane, treated with a solution of 1.11 g of 4-[trans-4-(4-methoxymethylidenecyclohexyl) cyclohexyl]-2-fluorobenzyl alcohol and subsequently 0.44 ml of methyl iodide was added. The mixture was held at reflux temperature for 1 hour, cooled, treated cautiously with water and the reaction mixture was extracted with ether. The organic phase was dried over sodium sulfate, filtered and the filtrate was evaporated. This gave 1.15 g of 4-[trans-4-(4-methoxymethylidenecyclohexyl)-cyclohexyl]-2-fluorobenzyl methyl ether as a yellowish oil, (purity in accordance with GC 100%).

j) A solution of 1.15 g of 4-[trans-4-(4-methoxymethylidenecyclohexyl)cyclohexyl]-2-fluorobenzyl methyl ether in 10 ml of tetrahydrofuran was treated with 2.5 ml of a 3N hydrochloric acid and stirred at reflux temperature for 30 minutes. The reaction solution was cooled, partitioned between methylene chloride and 10 percent sodium bicarbonate solution, the organic phase was dried over sodium sulfate, filtered and the filtrate was evaporated. This gave 1.11 g of 4-[trans-4-(4-formylcyclohexyl)cyclohexyl]-2-fluorobenzyl methyl ether (cis/trans=4:1).

k) A solution of 1.11 g of 4-[trans-4-(4-formylcyclohexyl)-cyclohexyl]-2-fluorobenzyl methyl ether (cis/trans=4:1) in 1.5 ml of methylene chloride was treated in succession with a few drops of triethylamine, 12 ml of methanol and 0.45 ml of 20 percent sodium hydroxide solution and stirred at room temperature for 30 minutes. Then, the reaction mixture was poured into 50 ml of water and extracted with methylene chloride. The organic phase was dried over sodium carbonate, filtered and the filtrate was evaporated. Crystallization from hexane gave 0.53 of pure 4-[trans-4-(trans-4-formylcyclohexyl)cyclohexyl]-2-fluorobenzyl methyl ether, m.p. 52°–54° C.

l) A suspension of 0.41 g of methyltriphenylphosphonium bromide in 10 ml of t.-butyl methyl ether was treated at 0° C. with 0.135 g of potassium t.-butylate. After 5 minutes, a solution of 0.25 g of 4-[trans-4-(trans-4-formylcyclohexyl) cyclohexyl]-2-fluorobenzyl methyl ether in 5 ml of potassium t.-butylate was added dropwise, the reaction mixture was stirred at 0° C. for a further 30 minutes, poured into 50 ml of water, extracted with ether, the organic phases were combined, dried over magnesium sulfate, filtered and the filtrate was evaporated. The residue was chromatographed on silica gel with methylene chloride and crystallized from methylene chloride/isopropanol and hexane/ isopropanol. This gave 0.1 65 g of 4-[trans-4-(trans-4-vinylcyclohexyl) cyclohexyl]-2-fluorobenzyl methyl ether with the following properties: m.p. (C/N): 30.9° C., cl.p. (N/I): 114.2° C.

The following compounds can be produced in an analogous manner:

4-[trans-4-(trans-4-(E)-Propenylcyclohexyl)cyclohexyl]-2-fluorobenzyl methyl ether 4-[trans-4-(trans-4-(E)-(1-butenyl)cyclohexyl)cyclohexyl]-2-fluorobenzyl methyl ether 4-[trans-4-(trans-4-(E)-(1-pentenyl)cyclohexyl)cyclohexyl]-2-fluorobenzyl methyl ether 4-{trans-4-[2-(trans-4-vinylcyclohexyl)ethyl]cyclohexyl}-2-fluorobenzyl methyl ether 4-{trans-4-[2-(trans-4-(E)-propenylcyclohexyl)ethyl]cyclohexyl}-2-fluorobenzyl methyl ether 4-{trans-4-[2-(trans-4-(E)-(1-pentenyl)cyclohexyl)ethyl]cyclohexyl}-2-fluorobenzyl methyl ether 4-[trans-4-(trans-4-vinylcyclohexyl)cyclohexyl]-2,6-difluorobenzyl methyl ether, m.p. (C/N): 67° C., cl.p. (N/I): 67.5° C.

4-[trans-4-(trans-4-(E)-propenylcyclohexyl)cyclohexyl]-2,6-difluorobenzyl methyl ether 4-[trans-4-(trans-4-(E)-(1-butenyl)cyclohexyl)cyclohexyl]-2,6-difluorobenzyl methyl ether 4-[trans-4-(trans-4-(E)-(1-pentenyl)cyclohexyl)cyclohexyl]-2,6-difluorobenzyl methyl ether 4-{trans-4-[2-(trans-4-vinylcyclohexyl)ethyl]cyclohexyl}-2,6-difluorobenzyl methyl ether 4-{trans-4-[2-(trans-4-(E)-propenylcyclohexyl)ethyl]cyclohexyl}-2,6-difluorobenzyl methyl ether 4-{trans-4-[2-(trans-4-(E)-(1-pentenyl)cyclohexyl)ethyl]cyclohexyl}-2,6-difluorobenzyl methyl ether 4-[trans-4-(trans-4-vinylcyclohexyl)cyclohexyl]-2-fluorobenzyl ethyl ether 4-[trans-4-(trans-4-(E)-(1-butenyl)cyclohexyl)cyclohexyl]-2-fluorobenzyl ethyl ether 4-[trans-4-(trans-4-(E)-(1-pentenyl)cyclohexyl)cyclohexyl]-2-fluorobenzyl ethyl ether 4-[trans-4-(trans-4-vinylcyclohexyl)cyclohexyl]-2,6-difluorobenzyl ethyl ether 4-[trans-4-(trans-4-(E)-propenylcyclohexyl)cyclohexyl]-2,6-difluorobenzyl ethyl ether 4-[trans-4-(trans-4-(E)-(1-butenyl)cyclohexyl)cyclohexyl]-2,6-difluorobenzyl ethyl ether 4-[trans-4-(trans-4-(E)-(1-pentenyl)cyclohexyl)cyclohexyl]-2,6-difluorobenzyl ethyl ether.

EXAMPLE 2

A solution of 2 g of 4-(trans-4-formylcyclohexyl)-3-fluorobenzyl methyl ether (produced analogously to Example 1 (a)–k)) and 1.05 g of 2-propyl-1,3-propanediol in 30 ml of benzene is heated to slight boiling with 35 mg of p-toluenesulfonic acid monohydrate. After neutralization of the solution with a few drops of triethylamine the mixture is washed with water, dried over sodium sulphate, filtered and the filtrate is evaporated. Chromatography of the residue on silica gel with methylene chloride and subsequent crystallization from hexane gives 4-[trans-4-(trans-5-propyl-1,3-dioxan-2-yl)cyclohexyl]-2-fluorobenzyl methyl ether.

In an analogous manner there can be produced:

4-[trans-4-(trans-5-Propyl-1,3-dioxan-2-yl)cyclohexyl]-2-fluorobenzyl methyl ether
4-[trans-4-(trans-5-butyl-1,3-dioxan-2-yl)cyclohexyl]-2-fluorobenzyl methyl ether
4-[trans-4-(trans-5-pentyl-1,3-dioxan-2-yl)cyclohexyl]-2-fluorobenzyl methyl ether
4-[trans-4-(trans-5-vinyl-1,3-dioxan-2-yl)cyclohexyl]-2-fluorobenzyl methyl ether
4-[trans-4-(trans-5-(E-)propenyl-1,3-dioxan-2-yl)cyclohexyl]-2-fluorobenzyl methyl ether
4-[trans-4-(trans-5-(3-butenyl)-1,3-dioxan-2-yl)cyclohexyl]-2-fluorobenzyl methyl ether
4-[trans-4-(trans-5-propyl-1,3-dioxan-2-yl)cyclohexyl]-2,6-difluorobenzyl methyl ether
4-[trans-4-(trans-5-butyl-1,3-dioxan-2-yl)cyclohexyl]-2,6-difluorobenzyl methyl ether
4-[trans-4-(trans-5-pentyl-1,3-dioxan-2-yl)cyclohexyl]-2,6-difluorobenzyl methyl ether
4-[trans-4-(trans-5-vinyl-1,3-dioxan-2-yl)cyclohexyl]-2,6-difluorobenzyl methyl ether
4-[trans-4-(trans-5-(E-)propenyl-1,3-dioxan-2-yl)cyclohexyl]-2,6-difluorobenzyl methyl ether
4-[trans-4-(trans-5-(3-butenyl)-1,3-dioxan-2-yl)cyclohexyl]-2,6-difluorobenzyl methyl ether
4-{2-[trans-4-(trans-5-propyl-1,3-dioxan-2-yl)cyclohexyl]ethyl}-2-fluorobenzyl methyl ether
4-{2-[trans-4-(trans-5-pentyl-1,3-dioxan-2-yl)cyclohexyl]ethyl}-2-fluorobenzyl methyl ether
4-{2-[trans-4-(trans-5-vinyl-1,3-dioxan-2-yl)cyclohexyl]ethyl}-2-fluorobenzyl methyl ether
4-{2-[trans-4-(trans-5-(3-butenyl)-1,3-dioxan-2-yl)cyclohexyl]ethyl}-2-fluorobenzyl methyl ether
4-{2-[trans-4-(trans-5-propyl-1,3-dioxan-2-yl)cyclohexyl]ethyl}-2,6-difluorobenzyl methyl ether
4-{2-[trans-4-(trans-5-pentyl-1,3-dioxan-2-yl)cyclohexyl]ethyl}-2,6-difluorobenzyl methyl ether
4-{2-[trans-4-(trans-5-vinyl-1,3-dioxan-2-yl)cyclohexyl]ethyl}-2,6-difluorobenzyl methyl ether
4-{2-[trans-4-(trans-5-(3-butenyl)-1,3-dioxan-2-yl)cyclohexyl]ethyl}-2,6-difluorobenzyl methyl ether
4-[trans-4-(trans-5-propyl-1,3-dioxan-2-yl)cyclohexyl]-2-fluorobenzyl ethyl ether
4-[trans-4-(trans-5-butyl-1,3-dioxan-2-yl)cyclohexyl]-2-fluorobenzyl ethyl ether
4-[trans-4-(trans-5-pentyl-1,3-dioxan-2-yl)cyclohexyl]-2-fluorobenzyl ethyl ether
4-[trans-4-(trans-5-propyl-1,3-dioxan-2-yl)cyclohexyl]-2-fluorobenzyl allyl ether
4-[trans-4-(trans-5-butyl-1,3-dioxan-2-yl)cyclohexyl]-2-fluorobenzyl allyl ether
4-[trans-4-(trans-5-pentyl-1,3-dioxan-2-yl)cyclohexyl]-2-fluorobenzyl allyl ether.

EXAMPLE 3 a) A suspension of 20 g of 4-[trans-4-(trans-4-propylcyclohexyl)cyclohexyl]-2-fluorobenzonitrile in 400 ml of glacial acetic acid is treated with 200 ml of 50 percent sulfuric acid and heated to reflux temperature for 20 hrs. Then, the reaction mixture is cooled, adjusted to pH 4 with solid sodium hydroxide and extracted with methylene chloride. The organic phases are combined, washed with water, dried over magnesium sulfate, filtered and the filtrate is evaporated. This gives 4-[trans-4-(trans-4-propylcyclohexyl)cyclohexyl]-2-fluorobenzoic acid.

b) 7.8 g of 4-[trans-4-(trans-4-propylcyclohexyl)cyclohexyl]-2-fluorobenzoic acid are added to a suspension of 4.5 g of lithium aluminium hydride in 150 ml of dry ether and the mixture is stirred under reflux for 23 hrs. The suspension is cooled to 0° C., treated cautiously with 40 ml of water and then with 150 ml of 3N sulfuric acid, extracted with ether and the organic phase is dried over sodium sulfate, filtered and the filtrate is evaporated. Chromatography of the residue on silica gel with methylene chloride/acetone (95:5) gives 4-[trans-4-(trans-4-propylcyclohexyl)cyclohexyl]-2-fluorobenzyl alcohol.

c) 1.2 g of sodium hydride dispersion (in oil, about 50 percent) is washed with hexane and then treated with a solution of 3.33 g of 4-[trans-4-(trans-4-propylcyclohexyl)cyclohexyl]-2-fluorobenzyl alcohol. Thereupon, 1.32 ml of methyl iodide are added and the mixture is held at reflux temperature for 1 hour, cooled, treated cautiously with water and extracted with ether. The organic phase is thereupon dried over sodium sulfate, filtered and the filtrate is evaporated. The residue is chromatographed on silica gel with methylene chloride and crystallized from methylene chloride/isopropanol and hexane/isopropanol. This gives 4-[trans-4-(trans-4-propylcyclohexyl)cyclohexyl]-2-fluorobenzyl methyl ether.

The following compounds can be produced in an analogous manner:

4-[trans-4-(trans-4-Ethylcyclohexyl)cyclohexyl]-2-fluorobenzyl methyl ether
4-[trans-4-(trans-4-butylcyclohexyl)cyclohexyl]-2-fluorobenzyl methyl ether
4-[trans-4-(trans-4-(3-butenyl)cyclohexyl)cyclohexyl]-2-fluorobenzyl methyl ether, m.p. C/N: 83.2° C., cl.p. (N/I): 139.9° C.
4-[trans-4-(trans-4-pentylcyclohexyl)cyclohexyl]-2-fluorobenzyl methyl ether
4-(trans-4-(trans-4-(4-pentenyl)cyclohexyl)cyclohexyl-2-fluorobenzyl methyl ether
4-[trans-4-(trans-4-ethylcyclohexyl)cyclohexyl]-2,6-difluorobenzyl methyl ether
4-[trans-4-(trans-4-propylcyclohexyl)cyclohexyl]-2,6-difluorobenzyl methyl ether
4-[trans-4-(trans-4-butylcyclohexyl)cyclohexyl]-2,6-difluorobenzyl methyl ether
4-[trans-4-(trans-4-(3-.butenyl)cyclohexyl)cyclohexyl]-2,6-difluorobenzyl methyl ether, m.p. (C/N): 54.9° C., cl.p. (N/I): 105° C.
4-[trans-4-(trans-4-pentylcyclohexyl)cyclohexyl]-2,6-difluorobenzyl methyl ether
4-[trans-4-(trans-4-(4-pentenyl)cyclohexyl)cyclohexyl]-2,6-difluorobenzyl methyl ether
4-{trans-4-[2-(trans-4-ethylcyclohexyl)ethyl]cyclohexyl}-2-fluorobenzyl methyl ether
4-{-trans-4-[2-(trans-4-propylcyclohexyl)ethyl]cyclohexyl}-2-fluorobenzyl methyl ether
4-{trans-4-[2-(trans-4-(3-butenyl)cyclohexyl)ethyl]cyclohexyl}-2-fluorobenzyl methyl ether
4-{trans-4-[2-(trans-4-(pentylcyclohexyl)ethyl]cyclohexyl}-2-fluorobenzyl methyl ether
4-{trans-4-[2-(trans-4-ethylcyclohexyl)ethyl]cyclohexyl}-2,6-difluorobenzyl methyl ether 4-{trans-4-[2-(trans-4-propylcyclohexyl)ethyl]cyclohexyl}-2,6-difluorobenzyl methyl ether 4-{trans-4-[2-(trans-4-(3-butenyl)cyclohexyl)ethyl]cyclohexyl}-2,6-difluorobenzyl methyl ether 4-{trans-4-[2-(trans-4-(pentylcyclohexyl)ethyl]cyclohexyl}-2,6-difluorobenzyl methyl ether 4-{2-[trans-4-(trans-4-ethylcyclohexyl)cyclohexyl]ethyl}-2-fluorobenzyl methyl ether 4-{2-[trans-4-(trans-4-propylcyclohexyl)cyclohexyl]ethyl}-2-fluorobenzyl methyl ether 4-{2-[trans-4-(trans-4-butylcyclohexyl)cyclohexyl]ethyl}-2-fluorobenzyl methyl ether 4-{2-[trans-4-(trans-4-pentylcyclohexyl)cyclohexyl]ethyl}-2-fluorobenzyl methyl ether 4-{2-[trans-4-(trans-4-vinylcyclohexyl)cyclohexyl]ethyl}-2-fluorobenzyl methyl ether 4-{2-[trans-4-(trans-4-(E)-propenylcyclohexyl)cyclohexyl]ethyl}-2-fluorobenzyl methyl ether 4-{2-[trans-4-(trans-4-(3-butenyl)cyclohexyl)cyclohexyl]ethyl}-2-fluorobenzyl methyl ether 4-{2-[trans-4-(trans-4-(4-pentenyl)cyclohexyl)cyclohexyl]ethyl}-2-fluorobenzyl methyl ether 4-{2-[trans-4-(trans-4-ethylcyclohexyl)cyclohexyl]ethyl}-2,6-difluorobenzyl methyl ether 4-{2-[trans-4-(trans-4-propylcyclohexyl)cyclohexyl]ethyl}-2,6-difluorobenzyl methyl ether 4-{2-[trans-4-(trans-4-butylcyclohexyl)cyclohexyl]ethyl}-2,6-difluorobenzyl methyl ether 4-{2-[trans-4-(trans-4-pentylcyclohexyl)cyclohexyl]ethyl}-2,6-difluorobenzyl methyl ether 4-{2-[trans-4-(trans-4-vinylcyclohexyl)cyclohexyl]ethyl}-2,6-difluorobenzyl methyl ether, m.p. (C/N): 56.6° C., cl.p. (N/I): 77° C.

4-{2-[trans-4-(trans-4-(E)-propenylcyclohexyl)cyclohexyl]ethyl}-2,6-difluorobenzyl methyl ether 4-{2-[trans-4-(trans-4-(3-butenyl)cyclohexyl)cyclohexyl]ethyl}-2,6-difluorobenzyl methyl ether, m.p. (C/N): 40.1° C., cl.p. (N/I): 101.2° C.

4-{2-[trans-4-(trans-4-(4-pentenyl)cyclohexyl)cyclohexyl]ethyl}-2,6-difluorobenzyl methyl ether 4-[trans-4-(trans-4-ethylcyclohexyl)cyclohexyl]-2-fluorobenzyl ethyl ether 4-[trans-4-(trans-4-butylcyclohexyl)cyclohexyl]-2-fluorobenzyl ethyl ether 4-[trans-4-(trans-4-pentylcyclohexyl)cyclohexyl]-2-fluorobenzyl ethyl ether 4-[trans-4-(trans-4-ethylcyclohexyl)cyclohexyl]-2,6-difluorobenzyl ethyl ether 4-[trans-4-(trans-4-propylcyclohexyl)cyclohexyl]-2,6-difluorobenzyl ethyl ether 4-[trans-4-(trans-4-butylcyclohexyl)cyclohexyl]-2,6-difluorobenzyl ethyl ether 4-[trans-4-(trans-4-pentylcyclohexyl)cyclohexyl]-2,6-difluorobenzyl ethyl ether 4-[trans-4-(trans-4-ethylcyclohexyl)cyclohexyl]-2-fluorobenzyl allyl ether 4-[trans-4-(trans-4-butylcyclohexyl)cyclohexyl]-2-fluorobenzyl allyl ether 4-[trans-4-(trans-4-pentylcyclohexyl)cyclohexyl]-2-fluorobenzyl allyl ether 4-[trans-4-(trans-4-ethylcyclohexyl)cyclohexyl]-2,6-difluorobenzyl allyl ether 4-[trans-4-(trans-4-propylcyclohexyl)cyclohexyl]-2,6-difluorobenzyl allyl ether 4-[trans-4-(trans-4-butylcyclohexyl)cyclohexyl]-2,6-difluorobenzyl allyl ether 4-[trans-4-(trans-4-pentylcyclohexyl)cyclohexyl]-2,6-difluorobenzyl allyl ether.

EXAMPLE 4

A mixture of 5.62 g of 4-(trans-4-propylcyclohexyl)-bromobenzene, 4.05 g of 3-fluoro-4-methoxymethylphenylboric acid, 430 mg of 5 percent palladium charcoal (DEGUSSA E 101 N/D), 50 ml of benzene, 25 ml of ethanol and 50 ml of 2M sodium carbonate solution is heated to boiling for 3 hrs., the catalyst is filtered off and the aqueous phase is separated. The organic phase is washed with 1N sodium hydroxide solution, saturated sodium hydrogen carbonate solution and with water, dried over sodium sulphate, filtered and the filtrate is evaporated. This gives 4-[4-(trans-4-propylcyohexyl)phenyl]-2-fluorobenzyl methyl ether.

In an analogous manner there can be produced

4-[4-(trans-4-Ethylcyclohexyl)phenyl]-2-fluorobenzyl methyl ether

4-[4-(trans-4-vinylcyclohexyl)phenyl]-2-fluorobenzyl methyl ether

4-[4-(trans-4-(3-butenyl)cyclohexyl)phenyl]-2-fluorobenzyl methyl ether

4-[4-(trans-4-pentylcyclohexyl)phenyl]-2-fluorobenzyl methyl ether

4-[4-(trans-4-ethylcyclohexyl)phenyl]-2,6-difluorobenzyl methyl ether

4-[4-(trans-4-vinylcyclohexyl)phenyl]-2,6-difluorobenzyl methyl ether, m.p. (K/I): 76° C.

4-[4-(trans-4-propylcyclohexyl)phenyl]-2,6-difluorobenzyl methyl ether

4-[4-(trans-4-(3-butenyl)cyclohexyl)phenyl]-2,6-difluorobenzyl methyl ether, m.p. (C/N): 62.8° C., cl.p. (N/I): 73.3° C.

4-[4-(trans-4-pentylcyclohexyl) phenyl]-2,6-difluorobenzyl methyl ether

4-{4-[2-(trans-4-propylcyclohexyl)ethyl]phenyl}-2-fluorobenzyl methyl ether

4-{4-[2-(trans-4-pentylcyclohexyl)ethyl]phenyl}-2-fluorobenzyl methyl ether

4-{4-[2-(trans-4-vinylcyclohexyl)ethyl]phenyl}-2-fluorobenzyl methyl ether

4-{4-[2-(trans-4-propylcyclohexyl)ethyl]phenyl}-2,6-difluorobenzyl methyl ether

4-{4-[2-(trans-4-pentylcyclohexyl)ethyl]phenyl}-2,6-difluorobenzyl methyl ether

4-{4-[2-(trans-4-vinylcyclohexyl)ethyl]phenyl}-2,6-difluorobenzyl methyl ether

4-[4-(trans-5-propyl-1,3-dioxan-2-yl)phenyl]-2-fluorobenzyl methyl ether

4-[4-(trans-5-butyl-1,3-dioxan-2-yl)phenyl]-2-fluorobenzyl methyl ether

4-[4-(trans-5-pentyl-1,3-dioxan-2-yl)phenyl]-2-fluorobenzyl methyl ether

4-[4-(trans-5-vinyl-1,3-dioxan-2-yl)phenyl]-2-fluorobenzyl methyl ether

4-[4-(trans-5-(E-)propenyl-1,3-dioxan-2-yl)phenyl]-2-fluorobenzyl methyl ether

4-[4-(trans-5-(3-butenyl)-1,3-dioxan-2-yl)phenyl]-2-fluorobenzyl methyl ether

4-[4-(trans-5-propyl-1,3-dioxan-2-yl)phenyl]-2,6-difluorobenzyl methyl ether

4-[4-(trans-5-butyl-1,3-dioxan-2-yl)phenyl]-2,6-difluorobenzyl methyl ether

4-[4-(trans-5-pentyl-1,3-dioxan-2-yl)phenyl]-2,6-difluorobenzyl methyl ether

4-[4-(trans-5-vinyl-1,3-dioxan-2-yl)phenyl]-2,6-difluorobenzyl methyl ether

4-[4-(trans-5-(E-)propenyl-1,3-dioxan-2-yl)phenyl]-2,6-difluorobenzyl methyl ether 4-[4-(trans-5-(3-butenyl)-1,3-dioxan-2-yl)phenyl]-2,6-difluorobenzyl methyl ether
4-[5-(trans-4-ethylcyclohexyl)pyridin-2-yl]-2-fluorobenzyl methyl ether
4-[5-(trans-4-propylcyclohexyl)pyridin-2-yl]-2-fluorobenzyl methyl ether
4-[5-(trans-4-pentylcyclohexyl)pyridin-2-yl]-2-fluorobenzyl methyl ether
4-[S-(trans-4-ethylcyclohexyl)pyrimidin-2-yl]-2-fluorobenzyl methyl ether
4-[5-(trans-4-propylcyclohexyl)pyrimidin-2-yl]-2-fluorobenzyl methyl ether
4-[5-(trans-4-pentylcyclohexyl)pyrimidin-2-yl]-2-fluorobenzyl methyl ether
4-[4-(trans-4-ethylcyclohexyl)phenyl]-2-fluorobenzyl ethyl ether
4-[4-(trans-4-vinylcyclohexyl)phenyl]-2-fluorobenzyl ethyl ether
4-[4-(trans-4-propylcyclohexyl)phenyl]-2-fluorobenzyl ethyl ether
4-[4-(trans-4-(3-butenyl)cyclohexyl)phenyl]-2-fluorobenzyl ethyl ether
4-[4-(trans-4-pentylcyclohexyl)phenyl]-2-fluorobenzyl ethyl ether
4-[4-(trans-4-ethylcyclohexyl)phenyl]-2,6-difluorobenzyl ethyl ether
4-[4-(trans-4-vinylcyclohexyl)phenyl]-2-fluorobenzyl ethyl ether
4-[$^4$-(trans-4-propylcyclohexyl)phenyl]-2,6-difluorobenzyl ethyl ether
4-[4-(trans-4-(3-butenyl)cyclohexyl)phenyl]-2,6-difluorobenzyl ethyl ether
4-[4-(trans-4-pentylcyclohexyl)phenyl]-2,6-difluorobenzyl ethyl ether
4-[4-(trans-4-ethylcyclohexyl)phenyl]-2-fluorobenzyl ethyl ether
4-[4-(trans-4-vinylcyclohexyl)phenyl]-2-fluorobenzyl ethyl ether
4-[4-(trans-4-propylcyclohexyl)phenyl]-2-fluorobenzyl ethyl ether
4-[4-(trans-4-(3-butenyl)cyclohexyl)phenyl]-2-fluorobenzyl ethyl ether
4-[4-(trans-4-pentylcyclohexyl)phenyl]-2-fluorobenzyl ethyl ether
4-[4-(trans-4-ethylcyclohexyl)phenyl]-2,6-difluorobenzyl ethyl ether
4-[4-(trans-4-vinylcyclohexyl)phenyl]-2-fluorobenzyl ethyl ether
4-[4-(trans-4-propylcyclohexyl)phenyl]-2,6-difluorobenzyl ethyl ether
4-[4-(trans-4-(3-butenyl)cyclohexyl) phenyl ]-2,6-difluorobenzyl ethyl ether
4-[4-(trans-4-pentylcyclohexyl)phenyl]-2,6-difluorobenzyl ethyl ether
4-[4-(trans-4-allylcyclohexyl)phenyl]-2-fluorobenzyl allyl ether
4-[4-(trans-4-vinylcyclohexyl)phenyl]-2-fluorobenzyl allyl ether
4-[4-(trans-4-propylcyclohexyl)phenyl]-2-fluorobenzyl allyl ether
4-[4-(trans-4-(3-butenyl)cyclohexyl)phenyl]-2-fluorobenzyl allyl ether
4-[4-(trans-4-pentylcyclohexyl)phenyl]-2-fluorobenzyl allyl ether
4-[4-(trans-4-allylcyclohexyl)phenyl]-2,6-difluorobenzyl allyl ether
4-[4-(trans-4-vinylcyclohexyl)phenyl]-2-fluorobenzyl allyl ether
4-[4-(trans-4-propylcyclohexyl)phenyl]-2,6-difluorobenzyl allyl ether
4-[4-(trans-$^4$-(3-butenyl)cyclohexyl)phenyl]-2,6-difluorobenzyl allyl ether
4-[4-(trans-4-pentylcyclohexyl)phenyl]-2,6-difluorobenzyl allyl ether

EXAMPLE 5

Binary mixtures (BM) with 4-(trans-4-pentylcyclohexyl)-benzonitrile were produced in order to investigate the properties of the compounds of formula I in mixtures. The threshold potential and the response times were measured at 22° C. in a TN cell (low bias tilt) having a plate separation of 8 μm; the 2.5-fold value of the threshold potential ($V_{10}$) was chosen as the operating voltage. The corresponding data for 4-(trans-4-pentyl-cyclohexyl)benzonitrile are: cl.p. (N-I) =54.6° C., $v_{10}$=1.62 V, $t_{on}$=22 ms, $t_{off}$=42 ms, Δn=0.120.

BM-1
  90 wt. % of 4-(trans-4-pentylcyclohexyl)benzonitrile
  10 wt. % of 4-[trans-4-(trans-4-vinylcyclohexyl)cyclohexyl]-2-fluorobenzyl methyl ether
  cl.p. (N/I): 59.3° C., $V_{10}$=1.67 V, $t_{on}$=29 ms, $t_{off}$=41 ms, Δn=0.123

BM-2
  80 wt. % of 4-(trans-4-pentylcyclohexyl)benzonitrile
  20 wt. % of 4-[trans-4-(trans-4-vinylcyclohexyl)cyclohexyl]-2-fluorobenzyl methyl ether
  cl.p. (N/I): 63.8° C., $V_{10}$=1.73 V, $t_{on}$=33 ms, $t_{off}$=43 ms, Δn=0.120

BM-3
  90 wt. % of 4-(trans-4-pentylcyclohexyl)benzonitrile
  10 wt. % of 4-[trans-4-(trans-4-vinylcyclohexyl)cyclohexyl]-2,6-difluorobenzyl methyl ether
  cl.p. (N/I): 55.5° C., $V_{10}$=1.58 V, $t_{on}$=29 ms, $t_{off}$=46 ms, Δn=0.120

BM-4
  80 wt. % of 4-(trans-4-pentylcyclohexyl)benzonitrile
  20 wt. % of 4-[trans-4-(trans-4-vinylcyclohexyl)cyclohexyl]-2,6-difluorobenzyl methyl ether
  cl.p. (N/I): 56.2° C., $V_{10}$=1.58 V, $t_{on}$=32 ms, $t_{off}$=53 ms, Δn=0.117

BM-5
  90 wt. % of 4-(trans-4-pentylcyclohexyl)benzonitrile
  10 wt. % of 4-[trans-4-(trans-4-(3-butenyl)cyclohexyl]-2-fluorobenzyl methyl ether
  cl.p. (N/I): 61.5° C., $V_{10}$=1.69, $t_{on}$=24.7 ms, $t_{off}$=40.8 ms, Δn=0.1228

BM-6
  80 wt. % of 4-(trans-4-pentylcyclohexyl)benzonitrile
  20 wt. % of 4-[trans-4-(trans-4-(3-butenyl)cyclohexyl]-2-fluorobenzyl methyl ether
  cl.p. (N/I): 68.4° C., $V_{10}$=1.78, $t_{on}$=24.7 ms, $t_{off}$=40.6 ms, Δn=0.1196

We claim:

1. A compound of the formula

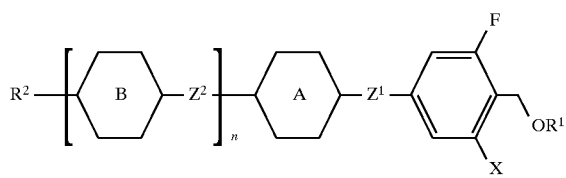

wherein

R₁ is $C_1$–$C_5$-alkyl or $C_3$–$C_5$-alkenyl; $C_1$–$C_5$ alkyl or $C_3$–$C_5$ alkenyl in which one $CH_2$ group is replaced by an oxygen atom; $C_1$–$C_5$ alkyl or $C_3$–$C_5$ alkenyl; or $C_1$–$C_5$ alkyl or $C_3$–$C_5$ alkenyl in which one $CH_2$ group is replaced by an oxygen atom;

X is H or F;

A and B each independently is trans-1,4-cyclo-hexylene, trans-1,3-dioxane-2,5-diyl, pyridine-2,5-diyl, pyrimidine-2,5-diyl, 1,4-phenylene or 1,4-phenylene substituted with 1 or 2 fluorine atoms;

$Z^1$ and $Z^2$ each independently is a single bond, —CH₂—CH₂—, —O—CH₂—, —CH₂—O—, —C≡C, —(CH₂)₄—, —O(CH₂)₃—, —(CH₂)₃O—, —CH=CH—CH₂O— or —CH=CH—(CH₂)₂—, and $Z^2$ also is —OCH₂—CH=CH— or —(CH₂)₂—CH=CH—; wherein at least one of groups $Z^1$ and $Z^2$ is a single bond;

n is 0 or 1; and $R^2$ is $C_2$–$C_{12}$-alkyl or $C_2$–$C_{12}$-alkenyl; $C_2$–$C_{12}$ alkyl or $C_2$–$C_{12}$ alkenyl in which one or more non-adjacent $CH_2$ groups is replaced by oxygen; $C_2$–$C_{12}$ alkyl or $C_2$–$C_{12}$ alkenyl in which one or more hydrogen atoms is replaced by a fluorine atom; or $C_2$–$C_{12}$ alkyl or $C_2$–$C_{12}$ alkenyl in which one or more non-adjacent $CH_2$ groups is replaced by an oxygen and in which one or more hydrogen atoms is replaced by a fluorine atom; and wherein $R^1$ is $C_1$–$C_5$ alkyl, $R_2$ is not $C_2$–$C_{12}$-alkyl.

2. A compound according to claim 1, wherein $R^1$ is methyl, ethyl or propyl.

3. A compound according to claim 1, wherein $R^2$ has 2 to 6 carbon atoms and is ethyl, propyl, butyl, pentyl, hexyl, vinyl, 1E-propenyl, 1E-butyl, 1E-pentenyl, 1E-hexenyl, 3-butenyl or 4-pentenyl.

4. A compound to claim 1, wherein $Z^1$ and $Z^2$ are each, independently, a single bond or —CH₂CH₂—.

5. A compound according to claim 1, wherein rings A and B are, independently, trans-1,4-cyclohexane, trans-1,3-dioxane-2,5-diyl or 1,4-phenylene.

6. A compound according to claim 1, 4-[trans-4-(trans-4-(3-butenyl)cyclohexyl) cyclohexyl]-2,6-difluorobenzyl methyl ether.

7. A liquid crystalline mixture comprising at least two components, wherein at least one component is a compound of the formula

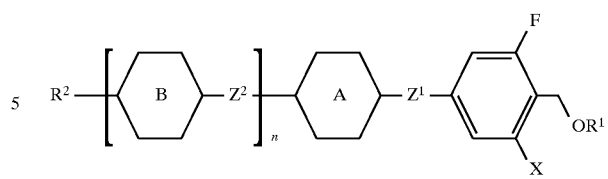

wherein $R^1$ is $C_1$–$C_5$-alkyl or $C_3$–$C_5$-alkenyl; $C_1$–$C_5$ alkyl or $C_3$–$C_5$ alkenyl in which one $CH_2$ group is replaced by an oxygen atom; $C_1$–$C_5$ alkyl or $C_3$–$C_5$ alkenyl in which at least one hydrogen atom is replaced by a fluorine atom; or $C_1$–$C_5$ alkyl or $C_3$–$C_5$ alkenyl in which one $CH_2$ group is replaced by an oxygen atom and;

X is H or F;

A and B each independently is trans-1,4-cyclo-hexylene, trans-1,3-dioxane-2,5-diyl, pyridine-2,5-diyl, pyrimidine-2,5-diyl, 1,4-phenylene or 1,4-phenylene substituted with 1 or 2 fluorine atoms;

$Z^1$ and $Z^2$ each independently is a single bond, —CH₂—CH₂—, —O—CH₂—, —CH₂—O—, —C≡C, —(CH₂)₄—, —O(CH₂)₃—, —(CH₂)₃)—, —CH=CH—CH₂O— or —CH=CH—(CH₂)₂—, and $Z^2$ also is —OCH₂—CH=CH— or —(CH₂)₂—CH=CH—; wherein at least one of groups $Z^1$ and $Z^2$ is a single bond;

n is 0 or 1; and $R^2$ is $C_2$–$C_{12}$-alkyl or $C_2$–$C_{12}$-alkenyl; $C_2$–$C_{12}$ alkyl or $C_2$–$C_{12}$ alkenyl in which one or more non-adjacent $CH_2$ groups is replaced by oxygen; $C_2$–$C_{12}$ alkyl or $C_2$–$C_{12}$ alkenyl in which one or more hydrogen atoms is replaced by a fluorine atom; or $C_2$–$C_{12}$ alkyl or $C_2$–$C_{12}$ alkenyl in which one or more non-adjacent $CH_2$ groups is replaced by an oxygen and in which one or more hydrogen atoms is replaced by a fluorine atom and wherein $R^1$ is $C_1$–$C_5$ alkyl, $R^2$ is not $C_2$–$C_{12}$ alkyl.

8. A liquid crystalline mixture according to claim 7, wherein the content of compounds of formula I is 1–70 wt. %.

9. A liquid crystalline mixture according to claim 7, wherein the content of compounds of formula I is 5–20 wt. %.

10. A compound of the formula

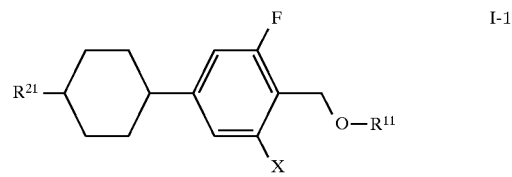

I-1

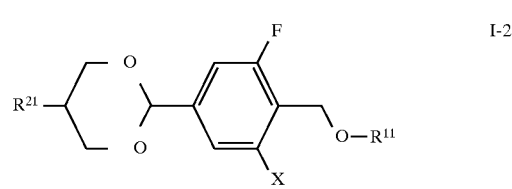

I-2

-continued
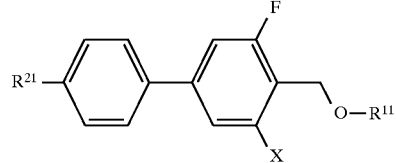 I-3
or
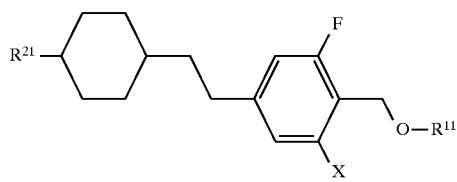 I-4
wherein
$R^{11}$ is $C_1$–$C_3$-alkyl;
X H or F; and
$R^{21}$ is $C_2$–$C_6$-alkyl or $C_2$–$C_6$-alkenyl.
11. A compound of the formula
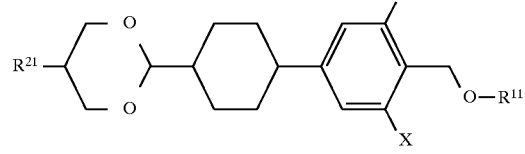 I-5
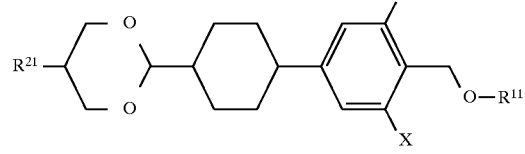 I-6
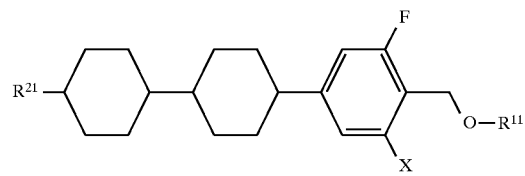 I-7
or
-continued
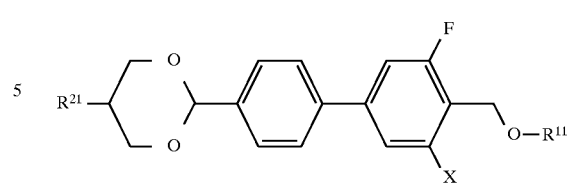 I-8
wherein
$R^{11}$ is $C_1$–$C_3$-alkyl;
X H or F; and
$R^{21}$ is $C_2$–$C_6$-alkyl or $C_2$–$C_6$-alkenyl.
12. A compound of the formula
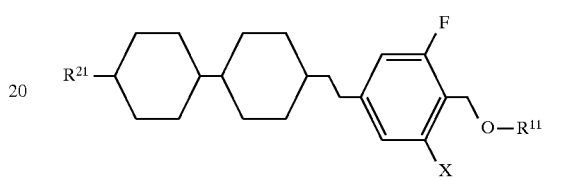 I-9
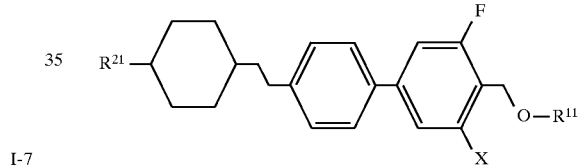 I-11
or
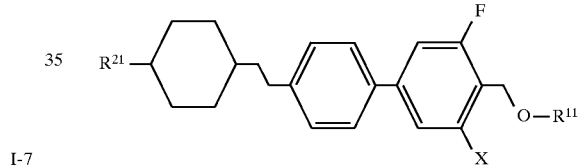 I-12
wherein
$R^{11}$ is $C_1$–$C_3$-alkyl;
X H or F; and
$R^{21}$ is $C_2$–$C_6$-alkyl or $C_2$–$C_6$-alkenyl.
* * * * *